United States Patent [19]

Cosgrove et al.

[11] Patent Number: 5,685,865

[45] Date of Patent: Nov. 11, 1997

[54] LOW VELOCITY AORTIC CANNULA

[75] Inventors: Delos M. Cosgrove, Hunting Valley; J. Fredrick Cornhill, Worthington, both of Ohio; Christopher M. Boykin, Saline, Mich.; Nelson L. Huldin, Pittsfield Township, Mich.; William G. O'Neill, Ann Arbor, Mich.

[73] Assignees: Minnesota Mining and Manufacturing Company, St. Paul, Minn.; Cleveland Clinic Foundation, Cleveland, Ohio

[21] Appl. No.: 318,207

[22] Filed: Aug. 3, 1993

Related U.S. Application Data

[63] Continuation of Ser. No. 21,811, Feb. 24, 1993, Pat. No. 5,354,288.

[51] Int. Cl.⁶ ............................................. A61M 5/00
[52] U.S. Cl. ...................................... 604/239; 604/264
[58] Field of Search .......................... 604/264, 272–275, 604/44, 46, 53, 280, 30, 31, 39, 239

[56] References Cited

U.S. PATENT DOCUMENTS

| | | | |
|---|---|---|---|
| 275,405 | 4/1883 | Parker . | |
| 609,280 | 8/1898 | King . | |
| 611,454 | 9/1898 | Longden . | |
| 829,952 | 9/1906 | Dean | 128/278 |
| 2,356,659 | 8/1944 | de Paiva Aguiar | 128/278 |
| 2,393,728 | 1/1946 | de P. Aguiar | 128/276 |
| 2,854,983 | 10/1958 | Baskin | 128/349 |
| 2,862,498 | 12/1958 | Weekes | 128/351 |
| 3,108,595 | 10/1963 | Overment | 128/350 |
| 3,397,699 | 8/1968 | Kohl | 128/349 |
| 3,568,659 | 3/1971 | Karnegis | 128/1 |
| 3,605,750 | 9/1971 | Sheridan et al. | 128/348 |
| 3,799,172 | 3/1974 | Szpur | 128/349 |
| 3,938,530 | 2/1976 | Santomieri | 128/349 |
| 3,955,573 | 5/1976 | Hansen et al. | 128/276 |
| 3,964,484 | 6/1976 | Reynolds et al. | 128/276 |
| 4,297,115 | 10/1981 | Johnson, Jr. | 55/302 |
| 4,321,920 | 3/1982 | Gillig | 128/239 |
| 4,375,816 | 3/1983 | Labianca | 604/8 |
| 4,437,856 | 3/1984 | Valli | 604/29 |
| 4,474,206 | 10/1984 | Cannon | 137/486 |

(List continued on next page.)

OTHER PUBLICATIONS

Advertising flyer for "Argyle ® Lighthouse Tip Vena Caval Catheter", by Sherwood Medical Company, dated 1985.
Charles C. Reed, Diane K. Clark, Chapter 19, "Cannulation", Chapter 23 Myocardial Protection, *Cardiopulmonary Perfusion*, Texas Medical Press, Inc., Houston, Texas, 1975.
"Atheroembolism From The Ascending Aorta", *The Journal of Thoracic and Cardiovascular Surgery*, C. Blauth et al., 1104–1111.

*Primary Examiner*—John D. Yasko
*Attorney, Agent, or Firm*—Armstrong, Teasdale, Schlafly & Davis

[57] ABSTRACT

A low velocity aortic cannula having a proximal end, a distal end, and a lumen therebetween for conducting blood, the distal end being adapted for insertion into the aorta during heart surgery to provide blood to the aorta. There is a diffuser at least partially blocking the distal end of the cannula, and a plurality of outlet openings in the side of the distal end of the cannula. In one embodiment the distal end of the cannula is closed with a cap, and the diffuser is a rounded cone extending generally upstream in the lumen. The outlet openings are located in the sidewall of the cannula. In a second embodiment of the invention, the diffuser has a helical configuration, and partially blocks the distal opening of the cannula. Additional openings are provided in the sidewall to permit flow. According to the method of this invention, an opening is formed in the aorta, the distal end of one of the embodiments of the cannula is inserted into the opening, and blood flow through the cannula is established.

19 Claims, 3 Drawing Sheets

U.S. PATENT DOCUMENTS

| | | | |
|---|---|---|---|
| 4,522,195 | 6/1985 | Schiff | 128/1 |
| 4,535,757 | 8/1985 | Webster, Jr. | 128/1 |
| 4,575,371 | 3/1986 | Nordqvist et al. | 604/96 |
| 4,580,568 | 4/1986 | Gianturco | 128/345 |
| 4,596,548 | 6/1986 | DeVries et al. | 604/4 |
| 4,617,019 | 10/1986 | Fecht et al. | 604/280 |
| 4,643,712 | 2/1987 | Kulik et al. | 604/4 |
| 4,655,745 | 4/1987 | Corbett | 604/49 |
| 4,680,029 | 7/1987 | Ranford et al. | 604/280 |
| 4,693,243 | 9/1987 | Buras | 128/207 |
| 4,710,180 | 12/1987 | Johnson | 604/239 |
| 4,787,882 | 11/1988 | Claren | 604/4 |
| 4,795,439 | 1/1989 | Guest | 604/43 |
| 4,795,446 | 1/1989 | Fecht | 604/264 |
| 4,801,297 | 1/1989 | Mueller | 604/280 |
| 4,802,819 | 2/1989 | Bevington et al. | 415/199.3 |
| 4,813,935 | 3/1989 | Haber et al. | 604/99 |
| 4,863,441 | 9/1989 | Lindsay et al. | 604/280 |
| 4,921,478 | 5/1990 | Solano et al. | 604/53 |
| 4,966,585 | 10/1990 | Gangemi | 604/131 |
| 5,021,044 | 6/1991 | Sharkawy | 604/53 |
| 5,084,033 | 1/1992 | O'Neill et al. | 604/264 |
| 5,147,332 | 9/1992 | Moorehead | 604/247 |
| 5,300,022 | 4/1994 | Klapper et al. | 604/35 |
| 5,354,288 | 10/1994 | Cosgrove et al. | 604/264 |

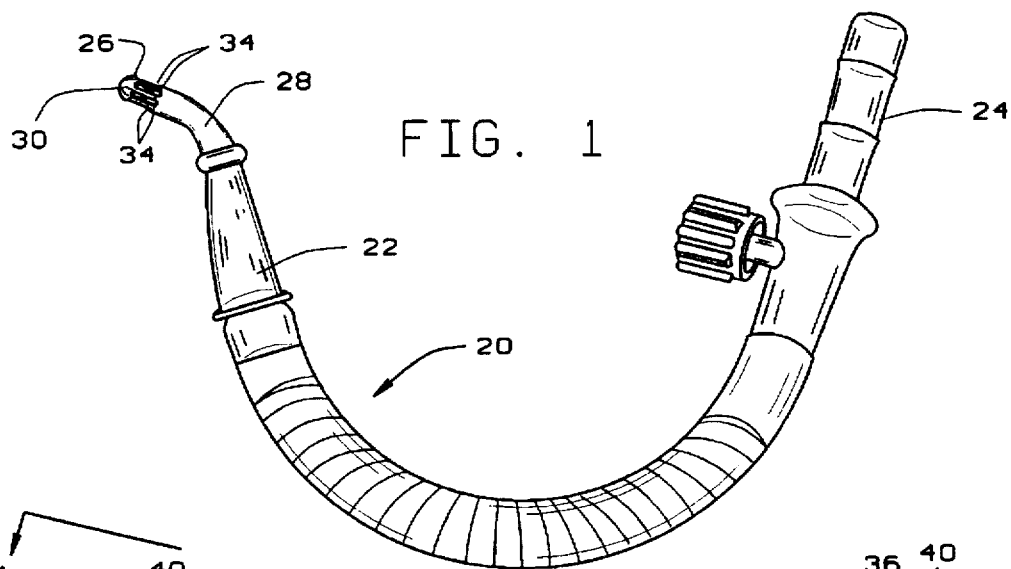
FIG. 1
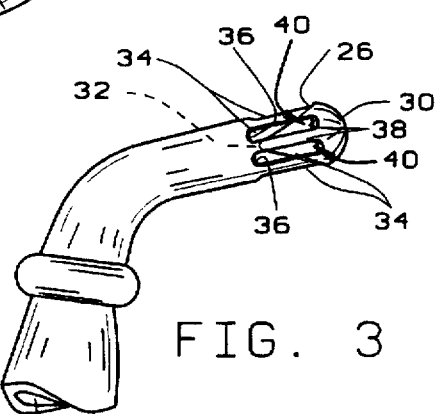
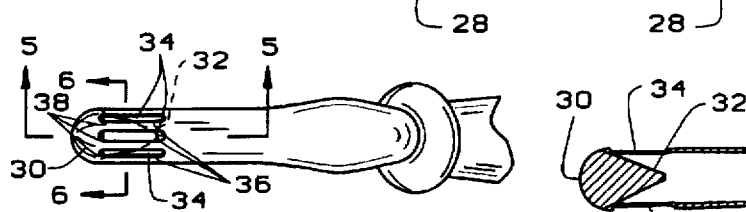
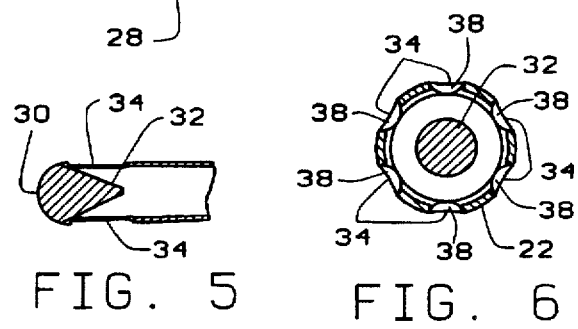
FIG. 2   FIG. 3   FIG. 4   FIG. 5   FIG. 6
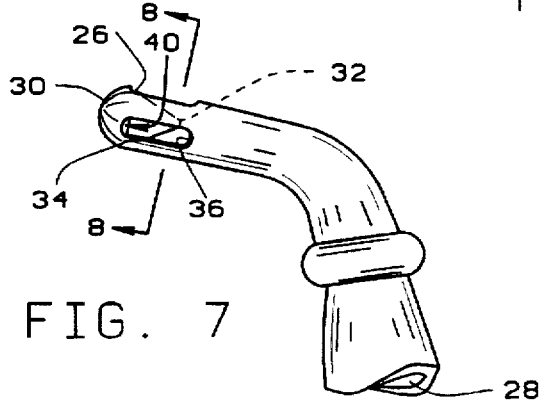
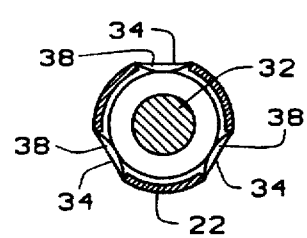
FIG. 7   FIG. 8

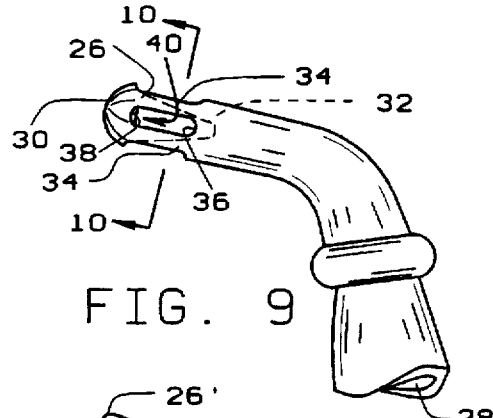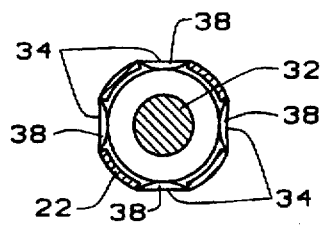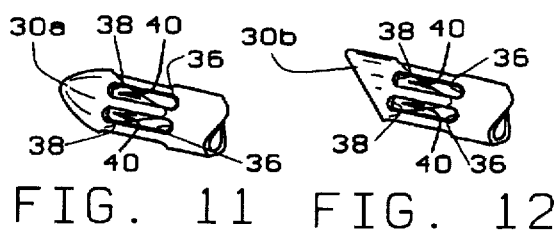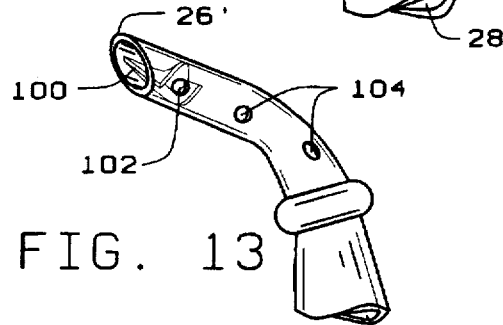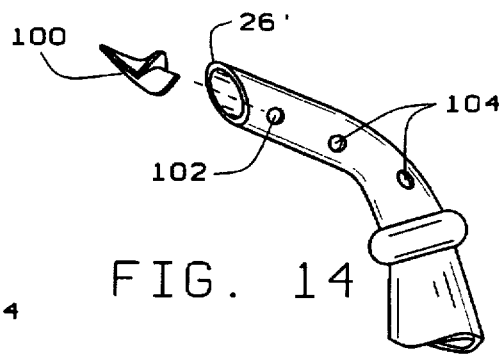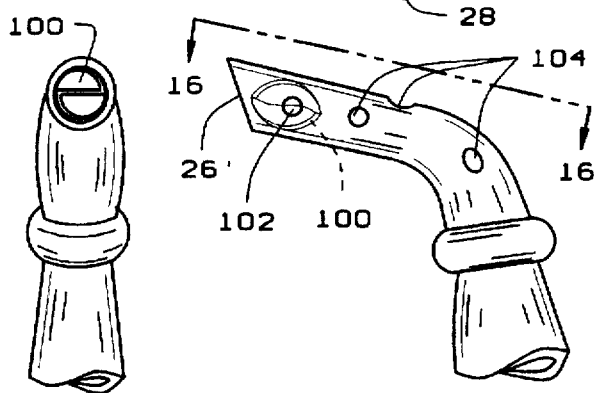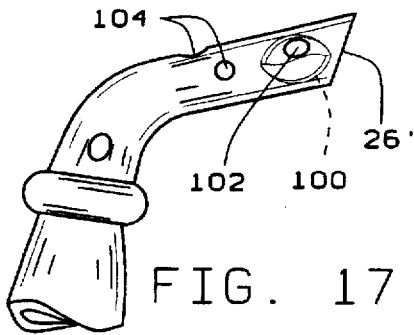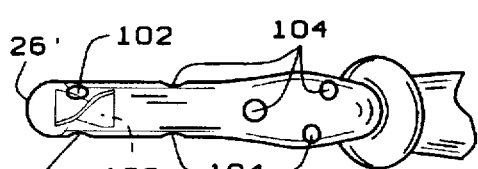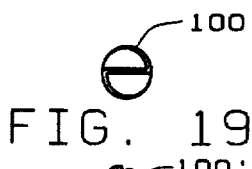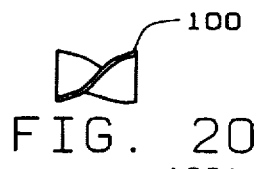

LOW VELOCITY AORTIC CANNULA

CROSS REFERENCE TO RELATED PATENT

This application is a continuation of application Ser. No. 08/21,811, filed Feb. 24, 1993, now U.S. Pat. No. 5,354,288.

This invention relates to a low velocity aortic cannula for use during heart surgery, and a method of delivering blood to the aorta using a low velocity aortic cannula.

BACKGROUND AND SUMMARY OF THE INVENTION

Aortic cannulas are used to return blood to the aorta while the heart is by-passed during heart surgery. These cannulas are purposely made with small diameters (typically six to eight millimeters, but even smaller for pediatric applications) to minimize the disruption to the aorta, which in many heart surgery patients have advanced complex atherosclerotic lesions with adherent blood thrombi. The flow velocities through these small diameter cannula must be very high in order to maintain a satisfactory blood flow rate of about five to seven liters per minute. In at least some styles of conventional aortic cannula now in use, this high velocity resulted in "jet" flow emanating from the distal end of the cannula, which acted as a nozzle. It is believed that the force of this narrow jet stream may dislodge atheromatous material and/or adherent thrombi from the walls of the aorta, causing embolisms. As surgical equipment and techniques improve, making heart surgery available to older and more seriously ill patients, thrombo-atheroembolisms affect an increasing number of patients due to the increasing extent of atherosclerosis with age.

The size of aortic cannula may be constrained by the constricted size of the aorta of the typical heart surgery patient. Moreover, the ability to diffuse flow is restricted by the fragility of the blood, which is easily damaged by the shear stresses associated with turbulence.

The aortic cannulas of the present invention are adapted to provide high volume flow at relatively lower flow velocities than the conventional aortic cannulas presently available, thereby reducing the jet flow and consequently reducing the incidence of thrombo-atheroembolisms. Generally aortic cannulas constructed according to the principles of this invention comprise a diffuser that blocks some or all of the flow through the distal end of the cannula, and a plurality of outlet openings in the sidewall of cannula adjacent the distal end to maintain flow volume.

According to a first embodiment of this invention, the distal end of the aortic cannula is substantially blocked with a cap, and there is a tapering, preferably conical, diffuser extending upstream inside the lumen of the cannula toward the proximal end of the cannula. There are outlet openings in the sidewall of the cannula that permit the blood deflected by the diffuser to flow out of the cannula.

According to a second embodiment of this invention, the distal end of the aortic cannula is partially blocked by a diffuser having helical splines. There are a plurality of openings in the sidewall of the cannula between the splines on the diffuser to permit blood to flow out of the cannula. Additional outlet openings can be provided in the sidewall of the cannula upstream of the diffuser to reduce back pressure and the flow velocity from the distal end of the cannula.

The outlet openings provide for increased flow, thereby reducing the flow velocity from the cannula. The openings allow the flow to quickly establish a stable, more uniform velocity flow. In the first embodiment, the diffuser diverts the flow out of the outlet openings, minimizing hemolysis or other damage to the blood. In the second embodiment, the diffuser reduces the flow through distal end of the cannula, preventing jetting by imparting angular momentum to the fluid, and diverts a portion of the flow through the outlet openings in the sidewall surrounding the diffuser. Thus, the aortic cannula of the present invention reduces the high velocity jetting that can occur with some conventional aortic cannulas, while maintaining flow rate and minimizing damage to the blood.

These and other features and advantages will be in part apparent and in part pointed out out hereinafter.

BRIEF DESCRIPTION OF THE DRAWINGS

FIG. 1 is a side elevation view of a first embodiment of an aortic cannula constructed according to the principles of this invention;

FIG. 2 is a right side elevation view of the tip of the aortic cannula of the first embodiment;

FIG. 3 is a left side elevation view of the tip of the aortic cannula of the first embodiment;

FIG. 4 is a top plan view of the tip of the aortic cannula of the first embodiment;

FIG. 5 is a longitudinal cross-sectional view of the tip of the aortic cannula of the first embodiment taken along the plane of line 5—5 in FIG. 4;

FIG. 6 is a transverse cross-sectional view of the tip of the aortic cannula of the first embodiment, taken along the plane of line 6—6 in FIG. 4;

FIG. 7 is a side elevation view of a first alternate construction of the first embodiment of an aortic cannula;

FIG. 8 is a transverse cross-sectional view of the first alternate construction of the first embodiment of an aortic cannula, taken along the plane of line 8—8 in FIG. 7;

FIG. 9 is a side elevation view of a second alternate construction of the first embodiment of an aortic cannula;

FIG. 10 is a transverse cross-sectional view of the second alternate construction of the first embodiment, taken along the plane of line 10—10 in FIG. 9;

FIG. 11 is a partial side view of a third alternate construction of the first embodiment, showing an alternate configuration for the cap;

FIG. 12 is a partial side view of a fourth alternate construction of the first embodiment, showing an alternate configuration for the cap;

FIG. 13 is an enlarged perspective view of a second embodiment of an aortic cannula constructed according to the principles of this invention;

FIG. 14 is an enlarged perspective view of the tip of the aortic cannula of the second embodiment, with the helical diffuser removed;

FIG. 15 is an end elevation view of the tip of the aortic cannula of the second embodiment;

FIG. 16 is a right side elevation view of the tip of the aortic cannula of the second embodiment;

FIG. 17 is a left side elevation view of the tip of the aortic cannula of the second embodiment;

FIG. 18 is a top plan view of the tip of the aortic cannula of the second embodiment taken along the plane of line 18—18 in FIG. 16;

FIG. 19 is an end elevation of the diffuser employed in the second embodiment;

FIG. 20 is side elevation of the diffuser employed in the second embodiment;

FIG. 21 is an end elevation view of an alternate construction of the diffuser employed in the second embodiment;

FIG. 22 is a side elevation view of the alternate construction of the diffuser employed in the second embodiment;

FIG. 23 is a side elevation view of alternate construction of the aortic cannula of the second embodiment;

FIG. 24 is a side elevation view of the alternative construction shown in FIG. 23, rotated axially 90°;

FIG. 25 is a side elevation view of the alternative construction shown in FIG. 23, rotated axially 180°;

Corresponding reference numerals indicate corresponding parts throughout the several views of the drawings.

DETAILED DESCRIPTION OF THE PREFERRED EMBODIMENTS

Figure 26:
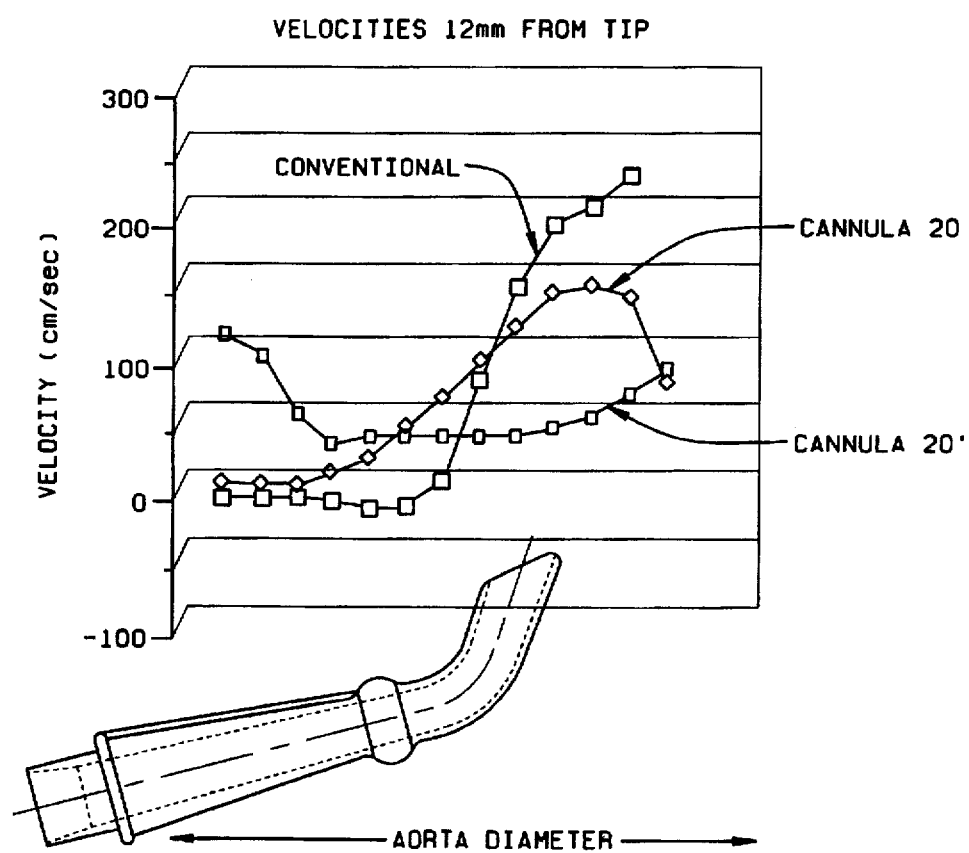
FIG. 26 is a graph showing the flow velocities created across the diameter of an aorta by a conventional aortic cannula, and by the aortic cannulas of the first and second embodiments, at a distance of 12 mm from the tip of the cannula.

A first embodiment of an aortic cannula constructed according to the principles of this invention is indicated generally as 20 in FIG. 1. The coronary cannula 20 comprises a generally tubular sidewall 22 having a proximal end 24 and a distal end 26, with a lumen 28 extending therebetween. As shown in FIG. 1, the cannula tapers toward the distal end so that the distal end has a diameter of between about 6 mm and 8 mm, to fit in the aorta of the patient. As shown in FIG. 2, the distal end 26 of the cannula 20 is closed with an end cap 30. The cap 30 may have a rounded, hemispherical shape, as shown in FIGS. 1–10 to facilitate the insertion of the distal end 26 of the cannula 20 into the aorta. The cap may also have a more conical configuration as shown in FIG. 11, or a rounded beveled configuration resembling a conventional aortic cannula tip, as shown in FIG. 12. The rounded shape of the tip also reduces the likelihood of damage to the aorta once the distal end 26 of the cannula 20 is placed in the aorta. The cap 30 and the diffuser (described below) are preferably molded in one piece with the cannula.

A tapering diffuser 32 extends from the end cap 30, inside the lumen 28 toward the proximal end 24 of the cannula 20. The diffuser 32 tapers toward the proximal end, i.e., in the upstream direction. The diffuser 32 preferably has a conical configuration, and is most preferably frustoconical, with a blunt, rounded apex so that the diffuser does not damage the blood flowing past it. The conical diffuser preferably has an apex angle of between about 20° and about 40° to smoothly diffuse the flow and impart a radially outward component to the flow. The diffuser 32 could also be pyramidal (or frustopyramidal), with a face of the pyramid oriented toward each of the outlet openings (described below).

A plurality of outlet openings 34 are formed in the sidewall of the cannula 20, adjacent the distal end 26. These openings 34 preferably have an arched configuration, with the curved portion 36 of each arch oriented toward the proximal end 24, i.e., oriented in the upstream direction. There are preferably six openings 34, equally spaced around the circumference of the distal end 26 of the cannula 20 (FIGS. 2–6). However, there could be three (FIGS. 7 and 8) or four (FIGS. 9 and 10) or some other suitable number of openings 34. The total area of the openings 34 is preferably greater than the area of the distal end opening in a conventional aortic cannula of the same diameter. The length of the openings 34 is preferably slightly greater than the length of the diffuser 32, so that the openings extend further upstream on the sidewall 22 than the diffuser projects in the lumen 28. Thus, the cross-sectional area of the lumen 28 taken up by the diffuser 32 is made up by the openings 34 so that in effect the diffuser causes no decrease in the cross-sectional area available for flow. Thus the diffuser does not interfere with flow or deleteriously increase back pressure; the diffuser merely redirects the flow.

As blood flows through the cannula 20 and reaches the distal end 26, the diffuser 32 imparts a radially outward component to the flow. The diffused flow is thus urged out through the openings 34, with a reduced velocity, because of the greater area of the openings 34, and a generally diffused state because of the diffuser 32 and the radially outward orientation of the openings 34. The smooth, continuous shape of the diffuser 32, the blunt, rounded configuration of the end of the diffuser, and the rounded configuration of the openings 32 all help to reduce turbulence in and disruption of blood flow and reduce hemolysis. The corners and edges in the cannula 20 are preferably rounded to minimize turbulence in and disruption of the flow, and promote a smooth, diffused flow while minimizing the increase in back pressure.

Deflectors 38 can be formed at the base 40 of each of the openings 34, opposite from the arched portions 36 of the openings. The deflectors 38 are preferably in the form of indentations in the cap 30 which further deflect the diffused flow radially outwardly. The deflectors have the shape of a portion of a sphere. The deflectors 38 splay out the flow, forming an "umbrella" pattern that establishes a stable flow in the aorta, reducing high velocity jetting and creating a more uniform flow velocity across the diameter of the aorta.

A second embodiment of an aortic cannula constructed according to the principles of this invention is indicated generally as 20' in FIGS. 13–18. The cannula 20' is similar to cannula 20, and corresponding reference numerals indicate corresponding parts throughout the several views of the drawings. The aortic cannula 20' comprises a sidewall 22, with a proximal end 24 and a distal end 26', and a lumen 28 extending therebetween. As shown in FIGS. 13–18, the distal end 26' of the cannula 20' has a diffuser 100 therein. The diffuser 100 has a helical configuration, as shown best in FIGS. 18 and 20. The diffuser 100 functions to slow the flow through the distal end 26' of the cannula 20', and to diffuse the direction of the flow. The diffuser 100 can be held in place by the tapering configuration of the distal end of the cannula 20', by adhesives, by ultrasonic welding, or by some other suitable means.

The sidewall of the cannula 20' surrounding the diffuser 100 has a plurality of outlet openings 102 therein to permit flow of blood from the cannula. The outlet openings 102 prevent a large back pressure from developing because of the diffuser 100 which partially blocks the outlet of the cannula. The outlet openings 102 also help maintain a satisfactory flow rate from the cannula. It is desirable that the openings be as large as possible, yet still fit between the splines on the diffuser, so that the openings do not form jets and to minimize hemolysis.

The diffuser 100 is preferably formed from a flat rectangular member with a single 180° twist therein, to give the diffuser a generally helical configuration. The diffuser 100 thus has two oppositely facing splines, formed by the edges of the member. However, in an alternative construction of the diffuser 100', shown in FIGS. 21 and 22, the diffuser has a more complex helical shape, with more splines. However, the greater the number of spines the smaller the openings 102 must be to fit between the splines. Additional outlet openings 104 may be provided upstream of the openings 102 to further reduce the back pressure and increase the flow.

An alternate construction of the distal end 26" of the cannula 20' of the second embodiment is shown on FIGS. 23–25. The distal end 26" has a blunt, rounded configuration. There is a helical diffuser 100 inside the distal end 26". Rather than circular outlet openings 102, the distal end has arcuate slots 106 and 108 extending diagonally through the sidewall of the cannula, on opposite sides. The concave shape of slot 100 faces distally, the concave shape of slot 108 faces proximal.

OPERATION

In operation, an opening is made into the aorta and the distal end of the cannula 20 or 20' is inserted into the aorta. The rounded configuration of cap 30 facilitates the insertion of cannula 20 into the aorta. The beveled configuration of the distal end of cannula 20' facilitates the insertion of the cannula in to the aorta. When the cannula 20 or 20' is secured in place, blood flow is initiated. Blood flows through the lumen 28 and out the outlet openings at the distal end 26 of the cannula.

In cannula 20, the blood encounters the blunt conical diffuser 32 which, by virtue of its low cone angle, gently redirects the flow radially outwardly, through the openings 34. Thus, rather than a jetting, axial flow experienced with conventional aortic cannulas, the cannula 20 provides a diffused flow that more quickly establishes a stable, more uniform velocity blood flow in the aorta. The cannula 20 preferably has deflectors 38 at the base of the openings that further deflect the flow radially outwardly. The flow properties of the blood are such that the deflectors create an "umbrella" flow pattern that more quickly establishes a uniform flow in the aorta.

In cannula 20' the diffuser 100 slows flow through the axial opening in the distal end of the cannula, forcing flow radially outwardly through the outlet openings 102 and 104. Thus the axial jetting is eliminated and blood fills the aorta through the openings 102 and 104 in the sidewall 22.

The flow velocity reduction achieved by the cannulas of this invention is illustrated in FIG. 26, which shows the flow velocities across the diameter of a model aorta, measured 12 mm from the tip of a conventional aortic cannula, 12 mm from the tip of an aortic cannula 20 of the first embodiment, and 12 mm from the tip of an aortic cannula 20' of the second embodiment. FIG. 23 shows that the flow velocities generated by a conventional cannula 12 mm from the tip are as high as 200 cm/sec, and vary considerably across the diameter of the aorta. However, with the cannula 20 of the first embodiment, the maximum flow velocity 12 mm from the tip is about 130 cm/sec, and the variation in the velocity across the diameter of the aorta is significantly reduced. Similarly, with the cannula 20' of the second embodiment, the maximum flow velocity 12 mm from the tip is about 100 cm/sec, and the variation in the velocity across the diameter of the aorta is also significantly reduced.

Figure 27:
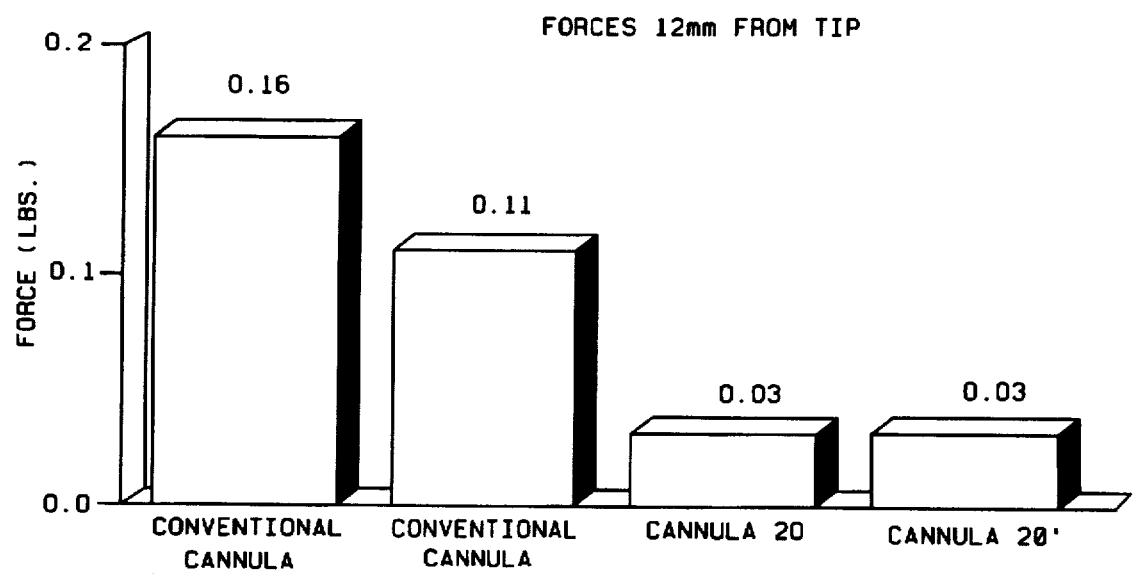
FIG. 27 is a chart showing the comparative forces generated by the flows from two styles of conventional aortic cannulas, and from the aortic cannulas of the first and second embodiments.

FIG. 27 illustrates the reduction in flow force achieved by the cannulas 20 and 20'. FIG. 24 shows the flow force measured 12 mm from the tip of two conventional cannulas as about 0.16 and 0.11 pounds, respectively. However the flow force measured 12 mm from the tip of cannula 20 is only 0.03 pounds, as is the flow force measured 12 mm from the tip of cannula 20'.

The cannulas 20 and 20' of this invention thus reduce maximum flow velocity, the variation in flow velocity, and the maximum flow force, while maintaining the overall flow rate. These reductions are believed to be significant in the reduction of thrombo-atheroembolisms, and other possible complications of heart surgery.

As various changes could be made in the above constructions without departing from the scope of the invention, it is intended that all matter contained in the above description or shown in the accompanying drawings shall be interpreted as illustrative and not in a limiting sense.

What is claimed is:

1. An improved aortic cannula having a sidewall with a proximal end, a distal end, and a lumen therebetween for conducting blood, the distal end being adapted for insertion into the aorta during heart surgery to provide blood to the aorta, the improvement comprising:

a cap for blocking axial flow from the distal end of the cannula;

a diffuser in the distal end of the lumen for diverting at least part of the flow through the cannula, the diffuser extending generally upstream in the lumen toward the proximal end of the cannula, and tapering in the upstream direction; and at least two outlet openings in the sidewall of the cannula adjacent the diffuser, the outlet openings comprising slots in the sidewall of the cannula, adjacent the distal end.

2. The improved aortic cannula according to claim 1 wherein the diffuser has a generally conical shape, with a blunt tip.

3. The improved aortic cannula according to claim 1 wherein the outlet openings comprise slots in the sidewall of the cannula, adjacent the distal end.

4. The improved aortic cannula according to claim 3 wherein the proximal ends of the slots are rounded.

5. The improved aortic cannula according to claim 3 wherein the slots extend proximally beyond the proximal end of the diffuser.

6. The improved aortic cannula according to claim 3 wherein there are three outlet openings in the sidewall.

7. The improved aortic cannula according to claim 3 wherein there are four outlet openings in the sidewall.

8. The improved aortic cannula according to claim 3 wherein there are six outlet openings in the sidewall.

9. The improved aortic cannula according to claim 1 further comprising a deflector distally below each outlet opening for deflecting at least a portion of the flow from each opening radially outwardly.

10. The improved aortic cannula according to claim 9 wherein the deflector comprises an indentation in the cap.

11. The improved aortic cannula according to claim 10 wherein the indentation has the shape of a portion of a sphere.

12. An aortic cannula for insertion into the aorta during heart surgery to provide blood to the aorta, the cannula comprising a sidewall having a proximal end and a distal end and a lumen therethrough, a cap at the distal end closing the lumen, a diffuser projecting proximally from the cap and tapering in the proximal direction, and outlet openings in the sidewall of the cannula adjacent the diffuser, allowing flow diverted by the diffuser to exit from the sides of the cannula.

13. The aortic cannula according to claim 12 wherein the diffuser is generally conical, having a blunt tip.

14. The aortic cannula according to claim 12 wherein the distal end of the cap has a rounded, hemispherical shape.

15. The aortic cannula according to claim 12 wherein the distal end of the cap has a rounded, conical shape.

16. The aortic cannula according to claim 12 wherein the distal end of the cap has a rounded, beveled shape.

17. The aortic cannula according to claim 12 wherein the outlet openings comprise slots in the sidewall, adjacent the distal end of the cannula.

18. The improved aortic cannula according to claim 17 wherein the proximal ends of the slots are rounded.

19. The improved aortic cannula according to claim 17 wherein the slots extend further proximally than the proximal end of the diffuser.

* * * * *

UNITED STATES PATENT AND TRADEMARK OFFICE
CERTIFICATE OF CORRECTION

PATENT NO. : 5,685,865
DATED : November 11, 1997
INVENTOR(S) : Cosgrove et al.

It is certified that error appears in the above-identified patent and that said Letters Patent is hereby corrected as shown below:

On the Cover Page, item [22] "Filed:", delete "Aug. 3, 1993" and insert therefor ---Oct. 7, 1994---.

In Column 6, Line 34, after "diffuser", delete ", the outlet openings comprising slots in the sidewall of the cannula, adjacent the distal end".

Signed and Sealed this

Fifteenth Day of September, 1998

BRUCE LEHMAN

Attest:

Attesting Officer

Commissioner of Patents and Trademarks